United States Patent [19]

Hanson et al.

[11] Patent Number: 5,175,181
[45] Date of Patent: Dec. 29, 1992

[54] IMIDAZOLYL/IMIDAZOLYLALKYL-N-TERMINAL AMINO HYDROXY

[75] Inventors: Gunnar J. Hanson, Skokie; John S. Baran, Winnetka; Dave Weissing, Lisle; Mark Russell, Skokie, all of Ill.

[73] Assignee: G. D. Searle & Co., Chicago, Ill.

[21] Appl. No.: 736,868

[22] Filed: Jul. 29, 1991

Related U.S. Application Data

[62] Division of Ser. No. 445,257, Dec. 4, 1989, abandoned.

[51] Int. Cl.$^5$ .................. A61K 31/415; C07D 233/66
[52] U.S. Cl. .................................... 514/400; 514/19; 514/396; 514/398; 514/399; 548/312.7; 548/333.5; 548/338.1; 548/338.5
[58] Field of Search ............... 548/336, 337, 341, 342, 548/343, 344; 514/19, 396, 398, 399, 400

[56] References Cited

FOREIGN PATENT DOCUMENTS

| | | |
|---|---|---|
| 128762 | 12/1984 | European Pat. Off. |
| 181110 | 5/1986 | European Pat. Off. |
| 189203 | 7/1986 | European Pat. Off. |
| 216539 | 1/1987 | European Pat. Off. |
| 229667 | 7/1987 | European Pat. Off. |
| 266950 | 10/1987 | European Pat. Off. |
| 300189 | 1/1989 | European Pat. Off. |
| 87/04349 | 7/1987 | PCT Int'l Appl. |

OTHER PUBLICATIONS

Umezawa et al., *J. Antibiot.* (Tokyo), 23, 259–262 (1970).
Gross et al., *Science*, 175, 656 (1971).
Boger et al., *Nature*, 303, 81–84 (1983).
Kokubu et al., *Biochem. Biophys. Res. Commun.*, 118, 929–933 (1984).
Castro et al., *FEBS Lett.*, 167, 273 (1984).
Hanson et al., *Biochem. Biophys. Res. Commun.*, 132, 155–161 (1985) and 146, 959–963 (1987).

*Primary Examiner*—Johann Richter
*Attorney, Agent, or Firm*—J. Timothy Keane; Paul D. Matukaitis

[57] ABSTRACT

Non-peptidyl compounds characterized generally as imidazolyl/imidazolylalkyl-N-terminal amino hydroxy β-amino acid derivatives are useful as renin inhibitors for treatment of hypertension. Compounds of particular interest are of the formula

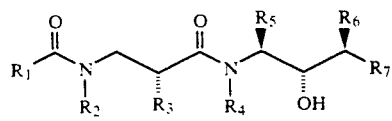

wherein $R_1$ is imidazolyl or imidazolylmethyl; wherein each of $R_2$ and $R_4$ is independently selected from hydrido and methyl; wherein $R_3$ is methyl or ethyl; wherein $R_5$ is cyclohexylmethyl; wherein $R_6$ is hydroxy; and wherein $R_7$ is isobutyl or ethyl; or a pharmaceutically-acceptable salt thereof.

12 Claims, No Drawings

IMIDAZOLYL/IMIDAZOLYLALKYL-N-TERMINAL AMINO HYDROXY

This is a divisional of application Ser. No. 07/445,257, filed Dec. 4, 1989, now abandoned.

FIELD OF THE INVENTION

Renin-inhibiting compounds are known for control of hypertension. Of particular interest herein are non-peptidyl compounds useful as renin inhibiting agents.

BACKGROUND OF THE INVENTION

Renin is a proteolytic enzyme produced and secreted into the bloodstream by the juxtaglomerular cells of the kidney. In the bloodstream, renin cleaves a peptide bond in the serum protein angiotensinogen to produce a decapeptide known as angiotensin I. A second enzyme known as angiotensin converting enzyme, cleaves angiotensin I to produce the octapeptide known as angiotensin II. Angiotensin II is a potent pressor agent responsible for vasoconstriction and elevation of cardiovascular pressure. Attempts have been made to control hypertension by blocking the action of renin or by blocking the formation of angiotensin II in the body with inhibitors of angiotensin I converting enzyme.

Classes of compounds published as inhibitors of the action of renin on angiotensinogen include renin antibodies, pepstatin and its analogs, phospholipids, angiotensinogen analogs, pro-renin related analogs and peptide aldehydes.

A peptide isolated from actinomyces has been reported as an inhibitor of aspartyl proteases such as pepsin, cathepsin D and renin [Umezawa et al, in *J. Antibiot.* (Tokyo), 23, 259–262 (1970)]. This peptide, known as pepstatin, was found to reduce blood pressure in vivo after the injection of hog renin into nephrectomized rats [Gross et al, *Science*, 175, 656 (1971)]. Pepstatin has the disadvantages of low solubility and of inhibiting acid proteases in addition to renin. Modified pepstatins have been synthesized in an attempt to increase the specificity for human renin over other physiologically important enzymes. While some degree of specificity has been achieved, this approach has led to rather high molecular weight hepta- and octapeptides [Boger et al, *Nature*, 303, 81 (1983)]; high molecular weight peptides are generally considered undesirable as drugs because gastrointestinal absorption is impaired and plasma stability is compromised.

Short peptide aldehydes have been reported as renin inhibitors [Kokubu et al. *Biochim. Biophys. Res. Commun.*, 118, 929 (1984); Castro et al. *FEBS Lett.*, 167, 273 (1984)]. Such compounds have a reactive C-terminal aldehyde group and would likely be unstable in vivo.

Other peptidyl compounds have been described as renin inhibitors. EP Appl. #128,762, published Dec. 18, 1984, describes dipeptide and tripeptide glycol-containing compounds as renin inhibitors [also see Hanson et al. Biochim. Biophys. Res. Commun., 132, 155–161 (1985), 146, 959–963 (1987)]. EP Appl. #181,110, published May 14, 1986, describes dipeptide histidine derivatives as renin inhibitors. EP Appl. #189,203, published Jul. 30, 1986, describes alkylnaphthyl-methylpropionyl-histidyl aminohydroxy alkanoates as renin inhibitors. EP Appl. #216,539, published Apr. 1, 1987, describes alkylnaphthylmethylpropionyl aminoacyl aminoalkanoate compounds as renin inhibitors orally administered for treatment of renin-associated hypertension. EP Appl. #229,667 published Jul. 22, 1987 describes acyl a-aminoacyl aminodiol compounds having a piperazinylcarbonyl or an alkylaminoalkylcarbonyl terminal group at the N-amino acid terminus, such as 2(S)-{[(1-piperazinyl)carbonyl]-oxy]-3-phenylpropionyl}-Phe-His amide of 2(S)-amino-1-cyclohexyl-3(R),4(S)-dihydroxy-6-methylheptane. PCT Application No. WO 87/04349 published Jul. 30, 1987 describes aminocarbonyl aminoacyl hydroxyether derivatives having an alkylamino-containing terminal substituent and which are described as having renin-inhibiting activity for use in treating hypertension. EP Appl. #300,189 published Jan. 25, 1989 describes amino acid monohydric derivatives having an alkylamino-alkylamino N-terminus which are mentioned as useful in treating hypertension. EP Appl. #266,950 published Nov. 5, 1988 describes heterocycliccarbonyl amino acid derivatives which are mentioned as having renin-inhibiting activity for use in treating hypertension.

DESCRIPTION OF THE INVENTION

Heterocyclic acyl aminodiol β-amino acid derivatives having utility as renin inhibitors for treatment of hypertension in mammals constitute a family of compounds of general Formula I:

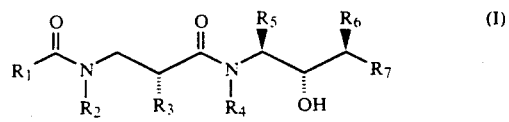

wherein $R_1$ is selected from aryl, aralkyl, heteroaryl and heteroaralkyl; wherein each of $R_2$ and $R_4$ is independently selected from hydrido and lower alkyl; wherein $R_3$ is selected from hydrido, alkyl, benzyl, cycloalkyl, cycloalkylalkyl, alkoxyalkyl, alkylthioalkyl and imidazolemethyl; wherein $R_5$ is selected from cycloalkyl, phenyl, lower alkyl, cycloalkylalkyl and phenylalkyl; wherein $R_6$ is selected from hydrido, hydroxy, alkoxy, amino, alkylamino, dialkylamino, lower alkyl and cycloalkyl; wherein $R_7$ is selected from hydrido, alkyl, haloalkyl, cycloalkylalkyl, alkylcycloalkyl, alkylcycloalkenyl and alkoxycarbonyl; wherein $R_6$ and $R_7$ may be taken together to form a carbocyclic or heterocyclic ring consisting of from 3 to about 8 ring members, which heterocyclic ring contains a hetero ring atom selected from oxygen atom, sulfur atom and NH; wherein each of $R_8$ and $R_9$ is independently selected from hydrido, alkyl, phenylalkyl, cycloalkyl, heterocyclicalkyl and phenyl; wherein $R_8$ and $R_9$ may be taken together to form a carbocyclic or heterocyclic ring consisting of from three to about eight ring members, which heterocyclic ring contains a hetero ring atom selected from oxygen atom, sulfur atom and >NH; and wherein any of the foregoing $R_1$ through $R_9$ substituents having a substitutable position may be substituted with one or more groups selected from alkyl, alkoxy, halo, haloalkyl, alkenyl, alkynyl and cyano; or a pharmaceutically-acceptable salt thereof.

A preferred family of compounds consists of those compounds of Formula I wherein $R_1$ is selected from aryl and aralkyl groups represented by

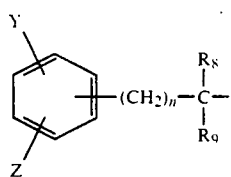

and wherein $R_1$ may be further selected from heteroaryl and heteroaralkyl represented by

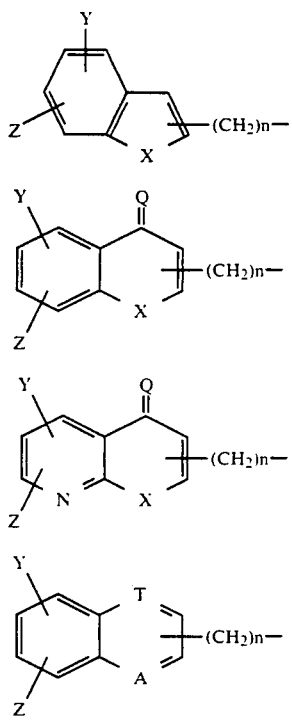

wherein X is selected from O, S, alkylamino and NH; wherein each of Y and Z is independently selected from lower alkyl, hydroxy, halo, alkoxy, carboxy, amino, alkylamino, dialkylamino, aryl, sulfhydryl and thioalkyl; wherein Q is selected from O and S; wherein each of T and A is independently selected from N and CH; wherein n is a number selected from zero through five, inclusive; wherein each of $R_2$ and $R_4$ is independently selected from hydrido and lower alkyl; wherein $R_3$ is selected from hydrido, alkyl, alkoxyalkyl, alkylthioalkyl and imidazolemethyl; wherein $R_5$ is selected from substituted or unsubstituted lower alkyl, cycloalkylalkyl and phenylalkyl; wherein $R_6$ is selected from hydrido, hydroxy, alkoxy, amino, alkylamino and dialkylamino; wherein $R_7$ is selected from hydrido, alkyl, haloalkyl, cycloalkylalkyl, alkylcycloalkyl, alkylcycloalkenyl and alkoxycarbonyl; wherein $R_6$ and $R_7$ may be taken together to form a carbocyclic or heterocyclic ring consisting of from 3 to about 6 members, which heterocyclic ring contains a hetero ring atom selected from oxygen atom, sulfur atom and NH; wherein each of $R_8$ and $R_9$ is independently selected from hydrido, alkyl, phenylalkyl, cycloalkyl, heterocyclicalkyl and phenyl; wherein $R_8$ and $R_9$ may be taken together to form a carbocyclic or heterocyclic ring consisting of from three to about six members, which heterocyclic ring contains a hetero ring atom selected from oxygen atom, sulfur atom and >NH; and wherein any of the foregoing $R^1$ through $R^9$ substituents may be substituted with one or more groups selected from alkyl, alkoxy, halo, haloalkyl, alkenyl, alkynyl and cyano; or a pharmaceutically-acceptable salt thereof.

A further preferred family of compounds consists of those compounds of Formula I wherein each of $R_2$ and $R_4$ is independently selected from hydrido and methyl; wherein $R_3$ is selected from hydrido, methyl, ethyl, methoxymethyl, methylthiomethyl and imidazolemethyl; wherein $R_5$ is selected from benzyl, cyclohexylmethyl, isobutyl and n-butyl; wherein $R_6$ is selected from hydrido, hydroxy, methoxy and dialkylamino; wherein $R_7$ is selected from isobutyl, ethyl, propyl and benzyl; wherein $R_6$ and $R_7$ may be taken together to form a carbocyclic or heterocyclic ring consisting of from 3 to about 6 members, which heterocyclic ring contains a hetero ring atom selected from oxygen atom, sulfur atom and >NH; wherein each of $R_8$ and $R_9$ is independently selected from hydrido, methyl, isopropyl, isobutyl, benzyl and imidazolemethyl; wherein $R_8$ and $R_9$ may be taken together to form a ring consisting of from three to about six members, which heterocyclic ring contains a hetero ring atom selected from oxygen atom, sulfur atom and >NH; wherein X is selected from alkylamino, NH, oxygen atom and sulfur atom; wherein each of Y and Z is independently selected from lower alkyl, hydroxy, halo, alkoxy, amino, alkylamino, dialkylamino, aryl, sulfhydryl and thioalkyl; wherein Q is oxygen atom; wherein each of T and A is independently selected from N and CH; wherein n is a number selected from zero through four.

A more preferred family of compounds consists of those compounds of Formula I wherein each of $R_2$ and $R_4$ is independently selected from hydrido and methyl; wherein $R_3$ is selected from methyl and ethyl; wherein $R_5$ is cyclohexylmethyl; wherein $R_6$ is hydroxy; wherein $R_7$ is selected from isobutyl and ethyl; wherein each of $R_8$ and $R_9$ is independently selected from hydrido, methyl and isopropyl; wherein X is selected from oxygen atom, methylamino >NH; wherein each of Y and Z is independently selected from Cl, F, methoxy and dimethylamino; wherein Q is oxygen atom; wherein each of T and A is independently selected from N and CH; wherein n is a number selected from zero through four.

The term "hydrido" denotes a single hydrogen atom (H) which may be attached, for example, to a carbon atom to form hydrocarbyl or methylene, for example, or attached to an oxygen atom to form a hydroxyl group. Where the term "alkyl" is used, either alone or within other terms such as "haloalkyl", "aralkyl" and "hydroxyalkyl", the term "alkyl" embraces linear or branched radicals having one to about twenty carbon atoms. Preferred alkyl radicals are "lower alkyl" radicals having one to about ten carbon atoms. Examples of which include methyl, ethyl, n-propyl, isopropyl, n-butyl,- sec-butyl, iso-butyl, tert-butyl, n-pentyl, neopentyl, n-hexyl, 1-methylhexyl, n-heptyl, 2-ethylheptyl, n-octyl, 3-propyloctyl, n-nonyl, 4-butylnonyl, n-decyl and the like. The term "cycloalkyl", embraces radicals having three to ten carbon atoms, such as cyclopropyl and cyclobutyl. "Alkylcycloalkyl" means a cyclized alkyl having from four to about nine ring carbon atoms being substituted with an alkyl group, preferably a lower alkyl group. The term "haloalkyl" embraces radicals wherein any one or more of the carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as bromochloromethyl group. Examples of a polyhaloalkyl are trifluoromethyl, 2,2,2-trifluoroethyl, perfluoroethyl and 2,2,3,3-tetrafluoropropyl groups. The term "aryl" embraces aromatic radicals such as phenyl, biphenyl and naphthyl. The term "aralkyl" embraces aryl-substituted alkyl radicals such as benzyl, diphenylmethyl and triphenylmethyl. The terms "benzyl" and "phenylmethyl" are interchangeable. The term "alkoxy" embraces linear or branched oxy-containing radicals having an alkyl portion of one to about ten carbon atoms, such as methoxy, ethoxy, isopropoxy and butoxy. The term "alkylthio" embraces radicals containing a linear or branched alkyl group of one to about ten carbon atoms attached to a divalent sulfur atom, such as a methythio group. The terms "aryloxy" and "arylthio" denote, respectively, aryl groups having an oxygen or sulfur atom through which the radical is attached to a nucleus, examples of which are phenoxy and phenylthio. The terms "sulfinyl" and "sulfonyl", whether used alone or linked to other terms, denote respectively, divalent radicals $>SO$ and $>SO_2$. The term "acyl" whether used alone, or within a term such as acyloxy, denotes a radical provided by the residue remaining after removal of hydroxy from an organic acid, examples of such radical being lower alkanoyl, such as acetyl, and benzoyl. The term "alkenyl" embraces linear or branched radicals having two to about twenty carbon atoms, preferably three to about ten carbon atoms, and containing at least one carbon-carbon double bond. The term "alkynyl" embraces linear or branched radicals having two to about twenty carbon atoms, preferably two to about ten carbon atoms, and containing at least one carbon-carbon triple bond. The terms "cycloalkenyl" and "cycloalkynyl" embrace cyclic radicals having three to about ten ring carbon atoms including, respectively, one or more double or triple bonds involving adjacent ring carbons. The terms "alkoxy" and "alkoxyalkyl" embrace linear or branched oxy-containing radicals each having alkyl portions of one to about ten carbon atoms, such as methoxy group. The "alkoxy" or "alkoxyalkyl" radicals may be further substituted with one or more halo atoms, such as fluoro, chloro or bromo, to provide haloalkoxy or haloalkoxyalkyl groups. The terms "heteroaryl", "aromatic heterocyclic group" and "fully-unsaturated heterocyclic group" embrace aromatic ring systems containing one or two hetero ring atoms selected from oxygen, nitrogen and sulfur in a ring system having five to about ten ring members; such ring system could be monocyclic, bicyclic, or fused ring system. The term "heteroaralkyl" embraces heteroaryl groups attached to the nucleus of Formula I through an alkyl group. The term "heterocyclic" embraces groups which may be saturated or partially unsaturated having three to eight ring members and which heterocyclic ring contains a hetero atom selected from oxygen atom, sulfur atom and NH, examples of which are thienyl, furanyl, pyridinyl and pyrimidyl. The term "heterocyclicalkyl" embraces heterocyclic groups attached to the nucleus of Formula I through an alkyl group.

Within this class of compounds of the invention are the pharmaceutically acceptable salts of the compounds of Formula I, including acid addition salts and base addition salts. The term "pharmaceutically-acceptable salts" embraces "pharmacologically-acceptable salts" commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, $\beta$-hydroxybutyric, malonic, galactaric and galacturonic acid. Suitable pharmaceutically-acceptable base addition salts of compounds of Formula I include metallic salts made from calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Based upon the foregoing, the meanings of the following terms should be readily discernible, namely, "cycloalkyl", "cycloalkylalkyl", "phenylalkyl" and "alkoxy".

Compounds of Formula I have been found to inhibit renin and thus limit the production of angiotensin I which, in turn, limits the production of angiotensin II in mammals. Angiotensin II is a potent vasoconstrictor and participates in the formation of aldosterone which regulates sodium and water balance in mammals. Thus, compounds of Formula I are therapeutically useful in methods for treating hypertension by administering to a hypertensive patient a therapeutically-effective amount of a compound of Formula I. The phrase "hypertensive patient" means, in this context, a mammalian subject suffering from the effects of hypertension or susceptible to a hypertensive condition if not treated to prevent or control such hypertension.

These compounds can be formulated into pharmaceutically-acceptable dosage forms by any of a number of well-known carriers or diluents. The compounds can be formulated using pharmaceutically-acceptable acid addition salts which are pharmacologically-acceptable and which can be used in a suitable hydrated form. The formulated compounds can be administered in oral dosage forms such as tablets, capsules, pills, powders, or granules. The compounds can also be administered intramuscularly, using forms known to the pharmaceutical art. In general, the preferred form of administration is oral. A therapeutically effective but non-toxic quantity of the compound is employed in treatment of high blood pressure in mammals. The dosage regimen for preventing or treating hypertension with the compounds of Formula I is selected upon consideration of a variety of factors, including the type, age, weight, sex, and medical condition of the patient, the severity of the hypertension, the route of administration, and the particular compound employed. Dosages of active compounds are ordinarily in the range from about 0.5 to about 100 mg/kg (active compound-to-body weight), and preferably from about 1.0 to about 20 mg/kg given orally or by injection.

Compounds of Formula I are also useful as diagnostic agents for identification of hypertension due to renin excess.

Compounds of Formula I can be administered as prodrugs. Preferably, esterification of one or more of the hydroxyl groups of the compounds of Formula I is accomplished with amino acids to make aminoesters, succinates to makes succinic acid esters, alkanoic acids to make carboxylic acid esters such as valerates, or phosphates to make phosphoric acid esters. Aminoesters and valerates of the Formula I compounds are more preferred.

Procedures for preparation of compounds of Formula I are set forth in the following "General Synthetic Scheme" and in the descriptions of the synthesis of specific compounds described in Examples 1–26 which follow thereafter.

The following examples are provided to illustrate the present invention and are not intended to limit the scope thereof. Those skilled in the art will readily understand that known variations of the conditions and processes of the following preparative procedures can be used to prepare these compounds. All temperatures expressed are in degrees Centigrade. Within the foregoing synthetic description and examples which fopllow, abbreviations have meanings as indicated below:

Boc = t-butyloxycarbonyl
i-Bu = isobutyl
Leu = leucine
Ac = acyl
Me = methyl
TFA = trifluoroacetic acid
THF = tetrahydrofuran
im = imidazole
AMBA = alpha-methyl-β-analine (also known as 2-R-methyl-3-aminopropionic acid)

Procedures for preparation of compounds of Formula I are set forth in the following "General Synthetic Scheme" and in the descriptions of the synthesis of specific compounds described in Examples 1–26 which follow thereafter. The synthesis of renin inhibitory compounds of Formula I may be summarized as follows: A suitably protected β-amino acid, preferably protected with a t-butyloxycarbonyl group for nitrogen, is coupled to a suitably protected aminodiol using a published procedure [F.M.F. Chen et al, *J. Org. Chem.*, 48, 2939 (1983)]. This conjugate is then treated with trifluoroacetic acid (or other appropriate agent) to remove the Boc group, and this resulting material is neutralized and coupled using Methods A, B, C or D (described below) to form heterocyclic or homocyclic carboxylic acid derivatives to produce the renin inhibitors of this invention. The substituents $R^1$ through $R^7$ represent groups as mentioned above in the general description of compounds within Formula I.

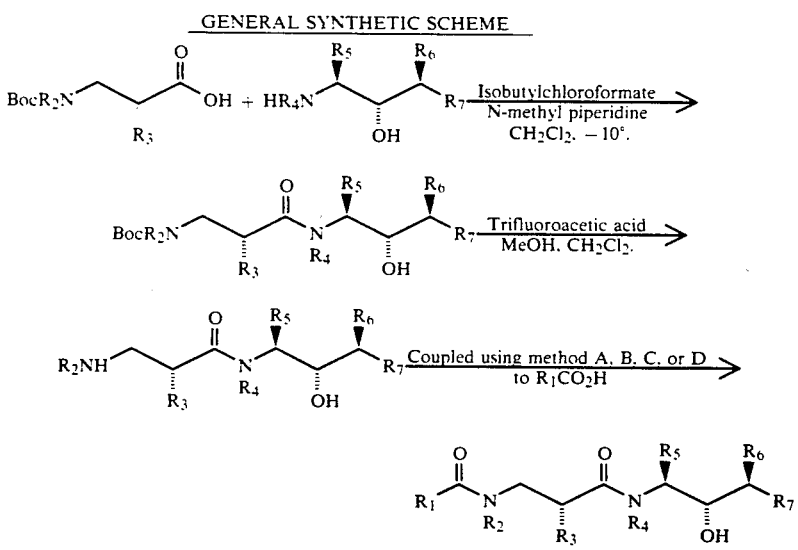

* Method A = Example 6
  Method B = Example 7
  Method C = Example 8
  Method D = Example 9,10

EXAMPLE 1

N-Boc-α-(R)-methyl-β-alanineamide of (2S,3R,4S)-2-amino-1-cyclohexyl-3,4-dihydroxy-6-methyl heptane To a solution of N-Boc-α-(R,S)-methyl-β-alanine (137 mg, 0.67 mmol) in methylene chloride (4 mL) at −10° C. was added N-methylpiperidine (61 mg, 0.61 mmol) followed by isobutylchloroformate (75 mg, 0.55 mmol). After stirring for 5 min, a solution of (2S,3R,4S)-2-amino-1-cyclohexyl-3,4-dihydroxy-6-methyl heptane (101 mg, 0.41 mmol) in methylene chloride (2 mL) was added. The resulting solution was stirred for 3 hours at −10° C., followed by 2 hours at room temperature at which time a white solid was isolated by filtration (60 mg. 34% yield): Rf=0.3 (5% MeOH/methylene chloride, silica gel); mp 197°-200°; 1H NMR (CDC13): consistent with proposed structure. Anal. calcd for $C_{23}H_{44}N_2O_5 + 0.25\ H_2O$: C, 63.77; H, 10.35; N, 6.46. Found: C, 63.84; H, 10.50; N, 6.45.

EXAMPLE 2

α-(R)-Methyl-β-alanineamide of (2S,3R,4S)-2-amino-1-cyclohexyl-3,4-dihydroxy-6-methylheptan e The title compound of Example 1 (53 mg, 0.12 mmol) was stirred with a mixture of trifluoroacetic acid and methanol (9:1, 5 mL). The resulting solution was allowed to stand at room temperature for 20 minutes, then the solvent was evaporated. The resulting oil was stirred for 2 hours with aqueous potassium carbonate (5%, 10 mL). This mixture was then extracted with ethyl acetate which was dried, filtered and evaporated to give the title compound (40 mg, 100%): Rf: 0.10 (5% MeOH/methylene chloride, silica gel). This material was used without further purification.

EXAMPLE 3

N-Methyl-N-Boc-α-(R)-methyl-β-alanine

To a solution of N-Boc-α-(R,S)-methyl-β-alanine (1.33 g, 6.5 mmol) in THF (80 ml)was added pentane washed sodium hydride(1.2 g, 60% in oil dispersion) followed by methyl iodide (2 ml, exess). The reaction mixture was stirred overnight and then poured into an iced solution of citric acid (0.5 N). The aqueous THF solution was extracted into ethyl acetate. Then the required acid was back extracted between ethyl acetate, sodium hydrogen carbonate and potassium hydrogen sulphate solutions. The organic extracts were dried (MgSO4) and evaporated to afford the title compound. (1.00 g, 71%), Anal: $C_{10}H_{19}NO_4 \cdot 0.3H_2O$, Calc: C, 53.94; H, 8.87; N, 6.29. Found, C, 54.02; H, 8.56; N, 6.63.

EXAMPLE 4

N-Methyl-N-Boc-α-(R)-methyl-β-alanineamide of (2S,3R, 4S)-2-amino-1-cyclohexyl -3,4-dihydroxy-6-methylheptane To a solution of N-Methyl-N-Boc-α-(R)-methyl-β-alanine (900 mg, 0.67 mmol) in methylene chloride (10 mL) at −10° C. was added N-methyl-piperidine (500 ul, 4.15 mmol) followed by isobutylchloroformate (450 mg, 3.3 mmol). After stirring for 5 min, a solution of (2S,3R,4S)-2-amino-1-cyclohexyl-3,4-dihydroxy-6-methylheptane (655 mg, 2.7 mmol) in methylene chloride (4 mL) was added. The resulting solution was stirred for 5 hours at −10° C. The solvent was evaporated in vacuo to afford an oily residue which was partitioned between ethyl acetate and saturated sodium bicarbonate. The organic layer was separated and dried (MgSO4). After evaporation the crude residue was dissolved in methanol (4 mL) to which potassium hydroxide solution (1 mL,1M) was added. The reaction mixture was stirred for 30 min, evaporated to dryness and the residue extracted into ethyl acetate. The organic extracts were washed with water, citric acid (0.5M) and saturated sodium bicarbonate solution and dried over MgSO4. Evaporation of the solvent gave a yellow residue which was recrystallized from diethyl ether to afford the title compound. (850 mg, 71% yield), Anal: $C_{24}H_{46}N_2O_5$, Calc, C, 65.12; H, 10.47; N, 6.33; Found, C, 65.10; H,10.37; N, 6.43.

EXAMPLE 5

N-Methyl-α-(R)-methyl-β-alanineamide of (2S,3R,4S)-2-amino-1-cyclohexyl-3,4-dihydroxy-6-methylheptane.

The title compound of Example 4 (820 mg, 1.86 mmol) was stirred with a mixture of trifluoroacetic acid and methanol (9:1, 5 mL). The resulting solution was allowed to stand at room temperature for 20 minutes, then the solvent was evaporated. The resulting oil was stirred for 2 hours with aqueous potassium carbonate (5%, 10 mL). This mixture was then extracted with ethyl acetate which was dried, filtered evaporated and precipitated from diethyl ethyl to afford the title compound. (580 mg, 92%). Anal: $C_{19}H_{38}N_2O_3$, Calc C, 64.59; H,11.18; N, 7.93; Found, C, 64.59; H, 10.50; N, 7.61.

EXAMPLE 6

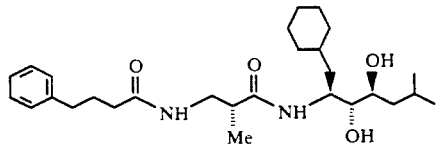

N-[3-[[1S,1R*-(cyclohexylmethyl)-2S*,3R*-dihydroxy-5-methylhexyl]amino]-2S*-methyl-3 -oxopropyl]benzenebutanamide To a stirred solution of phenylbutyric acid (60 mg, 0.183 mmol) in methylene chloride (2 mL) in an ice/salt bath was added N-methylpiperidine (0.08 mL, 2 eq) followed by isobutylchloroformate (40 mg, 1.6 eq). After 5 min, the title compound of Example 2 (60 mg, 0.183 mmol) in methylene chloride/methanol (1 ml/0.1 ml) was added and the reaction mixture was stirred at 0° C. for about 15 hours. The solvent was evaporated in vacuo to afford an oily residue which was partitioned between ethyl acetate and saturated sodium bicarbonate. The organic layer was separated and dried (MgSO4). After evaporation the crude residue was dissolved in methanol (4 mL) to which potassium hydroxide solution (1 mL,1M) was added. The reaction mixture was stirred for 30 min, evaporated to dryness and the residue extracted into ethyl acetate. The organic extracts were washed with water, citric acid (0.5M) and saturated sodium bicarbonate solution and dried over MgSO4. Evaporation of the solvent gave a yellow residue which was re-crystallized from diethyl ether to afford the title compound. (38 mg, 44% yield), Anal: $C_{28}H_{46}N_2O_4 \cdot 1.8\ H_2O$, Calc, C, 66.32; H, 9.86; N, 5.52. Found, C, 66.32; H, 9.18; N,5.57.

EXAMPLE 7

Method B

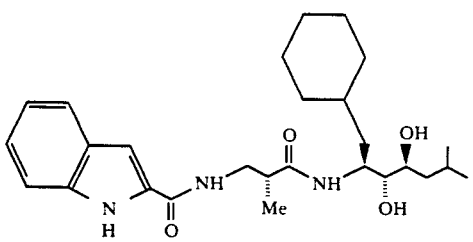

N-[3-[[1S,1R*-(cyclohexylmethyl)-2S*,3R*-dihydroxy-5-methylhexyl]amino]-2S*-methyl-3-oxopropyl]-1H-indole-2-carboxamide To a stirred solution of the title compound of Example 2 (150 mg, 0.46 mmol) in methylene chloride/methanol (5 ml/0.2 ml) was added triethylamine (0.2 ml, excess) followed by indole-2-oyl chloride (160 mg, 2 eq) and a catalytic amount of 4-dimethylaminopyridine. The reaction mixture was stirred at 0° C. for 15 hours. The solvent was evaporated in vacuo to afford an oily residue which was partitioned between ethyl acetate and saturated sodium bicarbonate. The organic layer was separated and dried (MgSO4). After evaporation the crude residue was dissolved in methanol (4 mL) to which potassium hydroxide solution (1 mL,1M) was added. The reaction mixture was stirred for 30 min, evaporated to dryness and the residue extracted into ethyl acetate. The organic extracts were washed with water, citric acid (0.5M) and saturated sodium bicarbonate solution and dried over MgSO4. Evaporation of the solvent gave a yellow residue which was recrystallized from diethyl ether to afford the title compound. (85 mg, 40% yield), Anal: $C_{27}H_{41}N_3O_4$, CalC, C, 68.72; H, 8.76; N, 8.91; Found. C, 68.62; H; 8.63; N, 8.86.

EXAMPLE 8

Method C

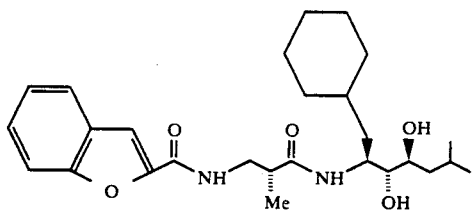

N-[3-[[1S,1R*-(cyclohexylmethyl)-2S*,3R*-dihydroxy-5-methylhexyl]amino]-2S*-methyl-3-oxopropyl]benzofuran-2-carboxamide To a stirred solution of the title compound of Example 2 (40 mg, 0.122 mmol) in methylene chloride/pyridine (1 ml/1 ml) at room temperature were added benzofuran-2-carboxylic acid anhydride (74 mg, 2 eq) and a catalytic amount of 4-dimethylaminopyridine. The reaction mixture was stirred for about 15 hours. The solvent was evaporated in vacuo to afford an oily residue which was partitioned between ethyl acetate and saturated sodium bicarbonate. The organic layer was separated and dried (MgSO4). After evaporation the crude residue was dissolved in methanol (4 mL) to which potassium hydroxide solution (1 mL,1M) was added. The reaction mixture was stirred for 30 min, evaporated to dryness and the residue extracted into ethyl acetate. The organic extracts were washed with water, citric acid (0.5M) and saturated sodium bicarbonate solution and dried over MgSO4 . Evaporation of the solvent gave a yellow residue which was recrystallized from diethyl ether to afford the title compound. (30 mg, 52% yield), Anal: $C_{27}H_{40}N_2O_5$.1.3 $H_2O$ , Calc: C, 65.38; H, 8.66; N, 5.65. Found, C, 65.32; H, 8.43; N, 5.55.

EXAMPLE 9

Method D

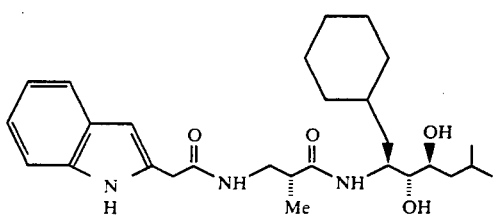

N-[3-[[1S,1R*-(cyclohexylmethyl)-2S*,3R*-dihydroxy-5-methylhexyl]amino]-2S*-methyl-3-oxopropyl]1H-indole-2-acetamide To a stirred solution of the title compound of Example 2 (60 mg, 0.183 mmol) a catalytic amount of 4-dimethylaminopyridine and indole-2-acetic acid (32 mg, 1 eq) in DMF (2 ml) was added dimethylaminopropyl3-ethylcarbodiimide (35 mg, 1 eq) at 0° C. The reaction mixture was stirred at room temperature for about 15 hours. The solvent was evaporated in vacuo to afford an oily residue which was partitioned between ethyl acetate and saturated sodium bicarbonate. The organic layer was separated and dried (MgSO4). After evaporation the crude residue was dissolved in methanol (4 mL) to which potassium hydroxide solution (1 mL,1M) was added. The reaction mixture was stirred for 30 min, evaporated to dryness and the residue extracted into ethyl acetate. The organic extracts were washed with water, citric acid (0.5M) and saturated sodium bicarbonate solution and dried over MgSO4 . Evaporation of the solvent gave a yellow residue which was recrystallized from diethyl ether to afford the title compound (65 mg, 72% yield), Anal: $C_{28}H_{43}N_3O_4$, Calc, C, 69.25; H, 8.92; N, 8.65; Found, C, 69.17; H, 9.13; N, 8.56.

EXAMPLE 10

Method D

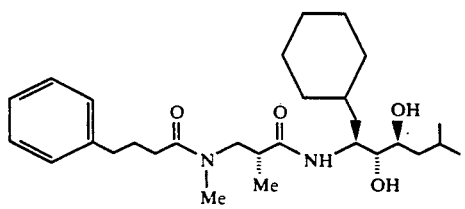

N-[3-[[1S,1R*-(cyclohexylmethyl)-2S*,3R*-dihydroxy-
5-methylhexyl]amino]-2S*-methyl-3
-oxopropyl]-N-methylbenzenebutanamide The title compound of Example 5 was coupled to 4-phenylbutyric acid using Method A. (56% yield), Anal: C29H48N2O4 .0.2 H2O. Calc, C, 70.75; H, 9.91; N, 5.69; Found, C, 70.83; H, 9.72; N, 5.77.

EXAMPLE 11

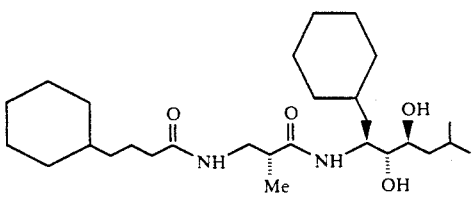

N-[3-[[1S,1R*-(cyclohexylmethyl)-2S*,3R*-dihydroxy-
5-methylhexyl]amino]-2S*-methyl-3
-oxopropyl]cyclohexanebutanamide The title compound of example 2 was coupled to 4-cyclohexylbutyric acid using Method A (58% yield). Anal: C28H52N2O4, Calc, C, 69.96; H, 10.90; N, 5.83; Found, C, 69.76; H, 10.95; N, 5.79.

EXAMPLE 12

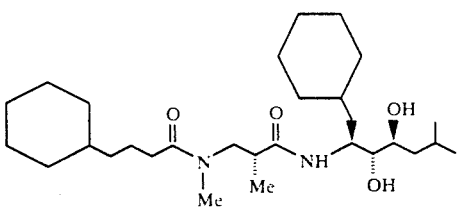

N [3-[[1S1R*-(cyclohexylmethyl)-2S*
3R*-dihydroxy-5-methylhexyl]amino]-2S*-methyl-3
-oxopropyl]-N-methylcyclohexanebutanamide The title compound of Example 5 was coupled to 4-cyclohexylbutyric acid using Method A. (70% yield) Anal: C29H54N2O4.0.2 H2O, Calc, C, 69.89; H, 11.00; N, 5.62; Found, C, 69.97; H. 11.00;

EXAMPLE 13

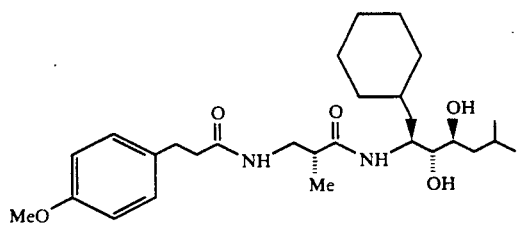

N-3-[[1S,1R*-(cyclohexylmethyl)-2S*,3R*-dihydroxy-
5-methylhexyl]amino]-2S*-methyl-3
-oxopropyl]-4-methoxybenzenepropanamide The title compound of Example 2 was coupled to 3-(4-methoxyphenylpropionic acid using Method A. (68% yield). Anal: C28H46N2O5, Calc, C, 68.54; H, 9.45; N, 5.71; Found, C, 68.24,; H, 9.58; N, 5.75.

EXAMPLE 14

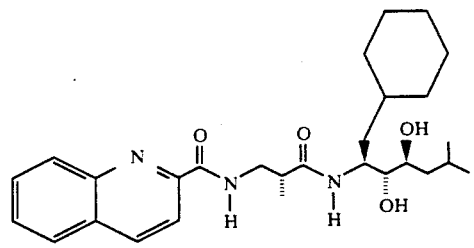

N-[3-[[1S,1R*-(cyclohexylmethyl)-2S*,3R*-dihydroxy-
5-methylhexyl]amino]-2S*-methyl-3
-oxopropyl]-2-quinaldylamide 27 mg (0.16 mmoles) of quinaldic acid was coupled to 30 mg (0.09 mmoles) of title compound of Example 2 using coupling Method A. Yield: 96%. 200 MHz NMR consistent with structure. C: cal'd, 69.54; found, 68.21. H: cal'd, 8.54; found, 8.84. N: cal'd, 8.69; found, 8.23. 95.34% pure by HPLC.

EXAMPLE 15

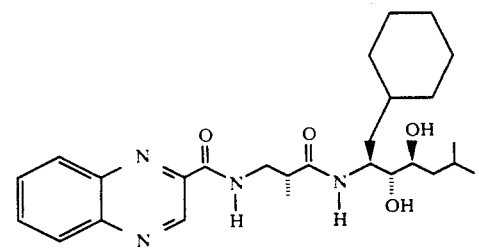

N-[3-[[1S,1R*-(cyclohexylmethyl)-2S*,3R*-dihydroxy-
5methylhexyl]amino]-2S*-methyl-3
-oxopropyl]-2-quinoxalinecarboxamide 86 mg (0.494 mmoles) of 2-quinoxalinecarboxylic acid was coupled to 101 mg (0.307 mmoles) of title compound of Example 2 using coupling Method A. Yield: 92%. 200 MHz NMR consistent with structure. C: cal'd, 66.92; found, 67.17. H: cal'd, 8.32; found, 8.38. N: cal'd, 11.56; found, 11.36.

EXAMPLE 16

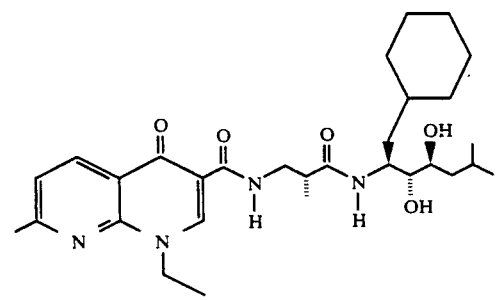

N-[3-[[1S,1R*-(cyclohexylmethyl)-2S*,3R*-dihydroxy-5-methylhexyl]amino]-2S*-methyl-3-oxopropyl]-nalidixylamide 117 mg (0.504 mmoles) of nalidixic acid was coupled to 104 mg (0.317 mmoles) of title compound of Example 2 using coupling Method A. Yield: 115 mg. 200 MHz NMR consistent with structure. C: cal'd, 66.39; found, 65.73. H: cal'd, 8.54; found, 8.48. N: cal'd, 10.32; found, 10.09. 91.70% pure by HPLC.

EXAMPLE 17

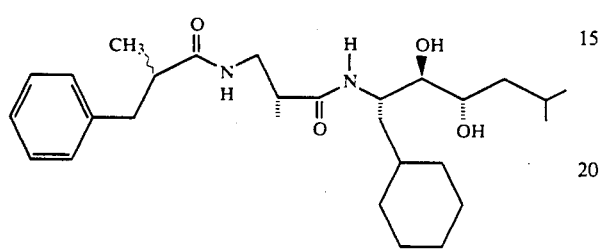

N-[3-[[1S,1R*-(cyclohexylmethyl)-2S*,3R*-dihydroxy-5-methylhexyl]amino]-2S*-methyl-3-oxopropyl]-(R,S)-α-methyl-hydrocinnamide 0.487 g (2.97 mmoles) of α-methyl-hydrocinnamic acid was coupled to 0.609 g (1.85 mmoles) of title compound of Example 2 using coupling Method A. Yield: 90 mg. 200 MHz NMR consistent with structure. C: cal'd, 70.85; found, 66.63. H: cal'd, 9.77; found, 9.81. N: cal'd, 5.90; found, 6.13.

EXAMPLE 18

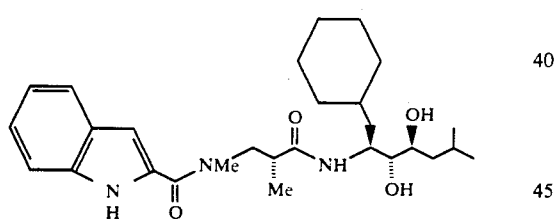

N-[3-[[1S,1R*-(cyclohexylmethyl)-2S*,3R*-dihydroxy-5-methylhexyl]amino]-2S*-methyl-3-oxopropyl]N-methyl-1H-indole-2-carboxamide The title compound of Example 5 was coupled to indole-2-carboxylic acid using Method B. (50%) Anal: $C_{28}H_{43}N_3O_4.0.2H_2O$ Calc: C, 68.14; H, 8.94; N 8.59; Found: C, 68.68; H, 8.88; N, 8.97.

EXAMPLE 19

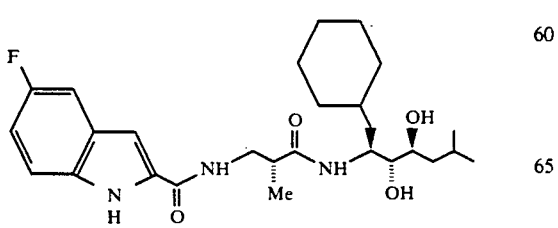

N-[3-[[1S,1R*-(cyclohexylmethyl)-2S*,3R*-dihydroxy-5methylhexyl]amino]-2S*-methyl-3-oxopropyl]-5-fluoro-1H-indole-2-carboxamide The title compound of Example 2 was coupled to 5-fluoroindole-2-carboxylic acid using Method A. 68% yield), Anal: $C_{27}H_{40}N_3O_4F.1.0\ H_2O$, Calc, C, 63.88; H, 8.34; N, 8.28; Found, C, 63.98; H, 7.96; N:8.04.

EXAMPLE 20

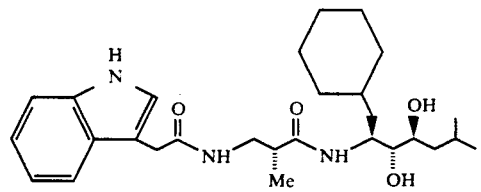

N-[3-[[1S,1R*-(cyclohexylmethyl)-2S*,3R*-dihydroxy-5-methylhexyl]amino]-2S*-methyl-3-oxopropyl]-1H-indole-3-carboxamide The title compound of Example 2 was coupled to indole-3-carboxylic acid using Method B. (58% yield), Anal: $C_{27}H_{41}N_3O_4$,Calc, C, 68.24; H, 8.78; N, 8.84; Found, C, 68.05; H, 8.26; N, 8.89.

EXAMPLE 21

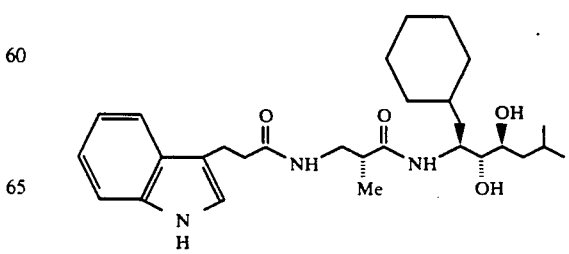

N-[3-[[1S,1R*-(cyclohexylmethyl)-2S*,3R*-dihydroxy-5-methylhexyl]amino]-2S*-methyl-3-oxopropyl]-1H-indole-3-acetamide The title compound of Example 2 was coupled to indole-3-acetic acid using Method B.(56% yield), Anal: $C_{28}H_{43}N_3O_4$ .0.7H_2O, Calc, C, 67.49; H, 8.98; N, 8.43; Found, C, 67.63; H, 8.96; N, 8.26.

EXAMPLE 22

N-[3-[[1S,1R*-(cyclohexylmethyl)-2S*,3R*-dihydroxy-5-methylhexyl]amino]-2S*-methyl-3 oxopropyl]-1H-indole-3-propanamide The title compound of Example 2 was coupled to indole-3-propionic acid using method A. (81% yield), Anal: $C_{29}H_{45}N_3O_4$, Calc, C, 69.71; H, 9.08; N, 8.41; Found, C, 69.26; H, 9.13; N, 8.28.

EXAMPLE 23

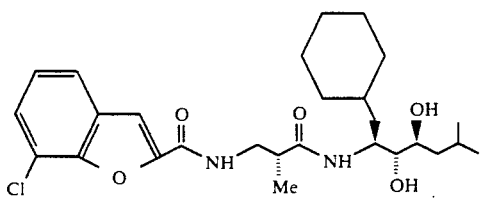

N-[3-[[1S,1R*-(cyclohexylmethyl)-2S*,3R*-dihydroxy-5-methylhexyl]amino]-2S*-methyl-3 oxopropyl]-7-chloro-benzofuran-2-carboxamide The title compound of Example 2 was coupled to 7-chlorobenzofuran-2-carboxylic acid using Method A. (38% yield), Anal: $C_{27}H_{39}N_2O_5Cl$, Calc,C:63.96, H:7.75, N:5.52, Found, C:64.24, H:8.36, N:5.64.

EXAMPLE 24

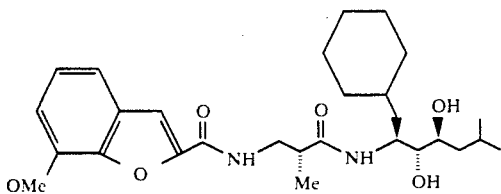

N-[3-[[1S,1R*-(cyclohexylmethyl)-2S*,3R*-dihydroxy-5-methylhexyl]amino]-2S*-methyl-3 -oxopropyl]-7-methoxybenzofuran-2-carboxamide The title compound of Example 2 was coupled to 7-methoxybenzofuran-2-carboxylic acid using Method A(40% yield). Anal: $C_{28}H_{42}N_2O_6$,Calc, C, 66.91; H, 8.42; N, 5.57; Found, C, 66.45; H, 8.34; N, 4.83.

EXAMPLE 25

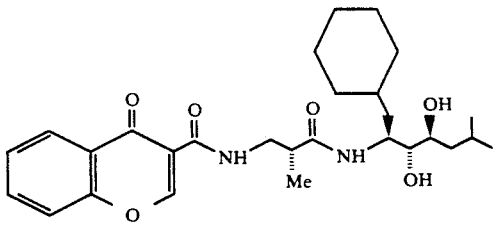

N-[3-[[1S,1R*-(cyclohexylmethyl)-2S*,3R*-dihydroxy-5-methylhexyl]amino]-2S*-methyl-3 -oxopropyl]-4-oxo-4H-1-benzopyran-3-carboxamide The title compound of Example 2 was coupled to chromone-3-carboxylic acid using Method A. (54% yield), Anal: $C_{28}H_{40}N_2O_6$, Calc, C, 67.18; H, 8.05; N, 5.60; Found, C, 66.82; H, 8.08; N, 5.47.

EXAMPLE 26

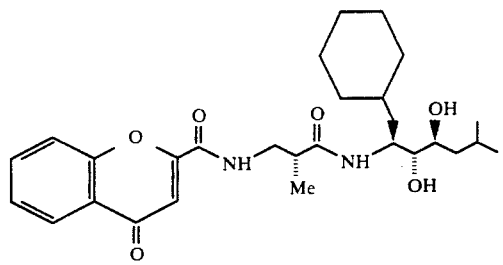

N-[3-[[1S,1R*-(cyclohexylmethyl)-2S*,3R*-dihydroxy-5-methylhexyl]amino]-2S*-methyl-3 -oxopropyl]-4-oxo-4H-1-benzopyran-2-carboxamide AMBA-diol was coupled to chromone-2-carboxylic acid using Method A (40% yield). Anal: $C_{28}H_{40}N_2O_6 \cdot 0.8H_2O$, Calc, C, 65.30; H, 8.14; N, 5.44; Found, C, 65.35; H, 7.74; N, 5.41.

BIOLOGICAL EVALUATION

Compounds of Formula I were evaluated as inhibitors of human renin in an in vitro assay. This human renin inhibition test has been previously described in detail [Papaioannou et al., *Clinical and Experimental Hypertension*, A7(9), 1243–1257 (1985)]. Human renin was obtained from the National Institute for Biologivcal Standards, London. An incubation mixture was prepared containing in a total volume of 0.25 mL 100 mM Tris-acetate buffer at pH 7.4, $25 \times 10^{-6}$ Goldblatt units of renin, 0.05 mL of plasma from human volunteers taking oral contraceptives, 6.0 mM sodium EDTA, 2.4 mM phenylmethyl sulfonyl fluoride, 1.5 mM 8-hydroxyquinoine, 0.4 mg/mL BSA, and 0.024 mg/mL neomycin sulfate. This mixture was incubated for two hours at 37° C. in the presence or absence of renin inhibitors. The produced angiotensin I was determined by radioimmunoassay (New England Nuclear kit). Test compounds to be assayed were dissolved in DMSO and diluted with 100 mM Tris-acetate buffer at pH 7.4 containing 0.5% BSA to the appropriate concentration. The final concentration of organic solvent in the reaction mixture was less than 1%. Control incubations at 37° C. were used to correct for effects of organic solvent on renin activity.

| In Vitro Inhibition Data | |
| --- | --- |
| Example # | IC$_{50}$ Human Renin (nM) |
| 6 | 125 |
| 7 | 26 |
| 10 | 115 |
| 11 | 180 |
| 12 | 23% inhibition @ $10^{-6}$ M |
| 13 | 30% inhibition @ $5 \times 10^{-7}$ M |
| 16 | 450 |
| 20 | 27% inhibition @ $10^{-5}$ M |
| 21 | 30% inhibition @ $10^{-6}$ M |
| 22 | 430 |
| 23 | 1800 |
| 24 | 3000 |
| 25 | 1100 |
| 26 | 520 |

Administration of compounds within Formula I to humans can be by any technique capable of introducing the compounds into the bloodstream of a human patient, including oral administration, and by intravenous, intramuscular and subcutaneous injections.

Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The active compound is usually administered in a pharmaceutically-acceptable formulation, although in some acute-care situations a compound of Formula I may be administered alone. Such formulations may comprise the active compound together with one or more pharmaceutically-acceptable carriers or diluents. Other therapeutic agents may also be present in the formulation. A pharmaceutically-acceptable carrier or diluent provides an appropriate vehicle for delivery of the active compound without introducing undesirable side effects. Delivery of the active compound in such formulations may be by various routes including oral, nasal, topical, buccal and sublingual, or by parenteral administration such as subcutaneous, intramuscular, intravenous and intradermal routes.

Formulations for oral administration may be in the form of capsules containing the active compound dispersed in a binder such as gelatin or hydroxypropylmethyl cellulose, together with one or more of a lubricant, preservative, surface-active or dispersing agent. Such capsules or tablets may contain controlled-release formulation as may be provided in a dispersion of active compound in hydroxypropylmethyl cellulose.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. Compound of the formula

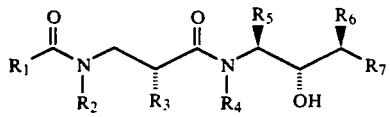

wherein $R_1$ is selected from imidazolyl and imidazolylalkyl; wherein each of $R_2$ and $R_4$ is independently selected from hydrido and lower alkyl; wherein $R_3$ is selected from hydrido, alkyl, benzyl, cycloalkyl, cycloalkylalkyl, alkoxyalkyl, alkylthioalkyl, imidazolyl and imidazolylalkyl; wherein $R_5$ is selected from cycloalkyl, phenyl, lower alkyl, cycloalkylalkyl and phenylalkyl; wherein $R_6$ is selected from hydrido, hydroxy, alkoxy, amino, alkylamino, dialkylamino, lower alkyl and cycloalkyl; wherein $R_7$ is selected from hydrido, alkyl, haloalkyl, cycloalkylalkyl, alkylcycloalkyl, alkylcycloalkenyl and alkoxycarbonyl; wherein $R_6$ and $R_7$ may further be taken together to form a carbocyclic ring consisting of from three to about eight ring members, or to form an imidazolyl or imidazolylalkyl group; and wherein any of the foregoing $R_1$ through $R_7$ substituents having a substitutable position may be substituted with one or more groups selected from alkyl, alkoxy, halo, haloalkyl, alkenyl, alkynyl and cyano; or a pharmaceutically-acceptable salt thereof.

2. Compound of claim 1 wherein $R_1$ is selected from imidazolyl, imidazolylmethyl and imidazolylethyl; wherein each of $R_2$ and $R_4$ is independently selected from hydrido and lower alkyl; wherein $R_3$ is selected from hydrido, alkyl, alkoxyalkyl, alkylthioalkyl, imidazolyl, imidazolylmethyl and imidazolylethyl; wherein $R_5$ is selected from substituted or unsubstituted lower alkyl, cycloalkylalkyl and phenylalkyl; wherein $R_6$ is selected from hydrido, hydroxy, alkoxy, amino, alkylamino and dialkylamino; wherein $R_7$ is selected from hydrido, alkyl, haloalkyl, cycloalkylalkyl, alkylcycloalkyl, alkylcycloalkenyl and alkoxycarbonyl; wherein $R_6$ and $R_7$ may further be taken together to form a carbocyclic ring consisting of from three to about six members, or to form an imidazolyl, imidazolylmethyl or imidazolylethyl group; and wherein any of the foregoing $R_1$ through $R_7$ substituents having a substitutable position may be substituted with one or more groups selected from alkyl, alkoxy, halo, haloalkyl, alkenyl, alkynyl and cyano; or a pharmaceutically-acceptable salt thereof.

3. Compound of claim 2 wherein each of $R_2$ and $R_4$ is independently selected from hydrido and methyl; wherein $R_3$ is selected from hydrido, methyl, ethyl, methoxymethyl, methylthiomethyl, imidazolyl and imidazlylmethyl; wherein $R_5$ is selected from benzyl, cyclohexylmethyl, isobutyl and n-butyl; wherein $R_6$ is selected from hydrido, hydroxy, methoxy and dialkylamino; wherein $R_7$ is selected from isobutyl, ethyl, propyl and benzyl; and wherein $R_6$ and $R_7$ may be taken together to form a carbocyclic ring consisting of from three to about six members, or to form imidazolyl or imidazolylmethyl; or a pharmaceutically-acceptable salt thereof.

4. Compound of claim 1 wherein each of $R_2$ and $R_4$ is independently selected from hydrido and methyl; wherein $R_3$ is selected from methyl and ethyl; wherein $R_5$ is cyclohexylmethyl; wherein $R_6$ is hydroxy; and wherein $R_7$ is selected from isobutyl and ethyl; or a pharmaceutically-acceptable salt thereof.

5. A pharmaceutical composition comprising a therapeutically-effective amount of a renin-inhibiting compound and a pharmaceutically-acceptable carrier or diluent, said renin-inhibiting compound selected from a family of compounds of the formula

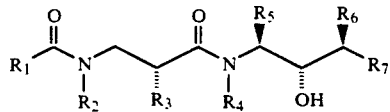

wherein R₁ is selected from imidazolyl and imidazolylalkyl; wherein each of R₂ and R₄ is independently selected from hydrido and lower alkyl; wherein R₃ is selected from hydrido, alkyl, benzyl, cycloalkyl, cycloalkylalkyl, alkoxyalkyl, alkylthioalkyl, imidazolyl and imidazolylalkyl; wherein R₅ is selected from cycloalkyl, phenyl, lower alkyl, cycloalkylalkyl and phenylalkyl; wherein R₆ is selected from hydrido, hydroxy, alkoxy, amino, alkylamino, dialkylamino, lower alkyl and cycloalkyl; wherein R₇ is selected from hydrido, alkyl, haloalkyl, cycloalkylalkyl, alkylcycloalkyl, alkylcycloalkenyl and alcoxycarbonyl; wherein R₆ and R₇ may further be taken together to form a carbocyclic ring consisting of from three to about eight ring members, or to form an imidazolyl or imidazolylalkyl group; and wherein any of the foregoing R₁ through R₇ substituents having a substitutable position may be substituted with one or more groups selected from alkyl, alkoxy, halo, haloalkyl, alkenyl, alkynyl and cyano; or a pharmaceutically-acceptable salt thereof.

6. The composition of claim 5 wherein R₁ is selected from imidazolyl, imidazolylmethyl and imidazolylethyl; wherein each of R₂ and R₄ is selected from hydrido and lower alkyl; wherein R₃ is selected from hydrido, alkyl, alkoxyalkyl, alkylthioalkyl, imidazolyl, imidazolylmethyl and imidazolylethyl; wherein R₅ is selected from substituted or unsubstituted lower alkyl, cycloalkylalkyl and phenylalkyl; wherein R₆ is selected from hydrido, hydroxy, alkoxy, amino, alkylamino and dialkylamino; wherein R₇ is selected from hydrido, alkyl, haloalkyl, cycloalkylalkyl, alkylcycloalkyl, alkylcycloalkenyl and alkoxycarbonyl; wherein R₆ and R₇ may further be taken together to form a carbocyclic ring consisting of from three to about six members, or to form an imidazolyl, imidazolylmethyl or imidazolylethyl group; and wherein any of the foregoing R₁ through R₇ substituents having a substitutable position may be substituted with one or more groups selected from alkyl, alkoxy, halo, haloalkyl, alkenyl, alkynyl and cyano; or a pharmaceutically-acceptable salt thereof.

7. The composition of claim 6 wherein each of R₂ and R₄ is independently selected from hydrido and methyl; wherein R₃ is selected from hydrido, methyl, ethyl, methoxymethyl, methylthiomethyl, imidazolyl and imidazolylmethyl; wherein R₅ is selected from benzyl, cyclohexylmethyl, isobutyl and n-butyl; wherein R₆ is selected from hydrido, hydroxy, methoxy and dialkylamino; wherein R₇ is selected from isobutyl, ethyl, propyl and benzyl; and wherein R₆ and R₇ may be taken together to form a carbocyclic ring consisting of from three to about six members, or to form imidazolyl or imidazolylmethyl; or a pharmaceutically-acceptable salt thereof.

8. The composition of claim 7 wherein each of R₂ and R₄ is independently selected from hydrido and methyl; wherein R₃ is selected from methyl and ethyl; wherein R₅ is cyclohexylmethyl; wherein R₆ is hydroxy; and wherein R₇ is selected from isobutyl and ethyl; or a pharmaceutically-acceptable salt thereof.

9. A therapeutic method for treating hypertension, said method comprising administering to a hypertensive patient a therapeutically-effective amount of a compound of the formula

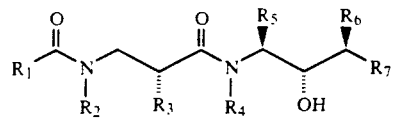

wherein R₁ is selected from imidazolyl and imidazolylalkyl; wherein each of R₂ and R₄ is independently selected from hydrido and lower alkyl; wherein R₃ is selected from hydrido, alkyl, benzyl, cycloalkyl, cycloalkylalkyl, alkoxyalkyl, alkylthioalkyl, imidazolyl and imidazolylalkyl; wherein R₅ is selected from cycloalkyl, phenyl, lower alkyl, cycloalkylalkyl and phenylalkyl; wherein R₆ is selected from hydrido, hydroxy, alkoxy, amino, alkylamino, dialkylamino, lower alkyl and cycloalkyl; wherein R₇ is selected from hydrido, alkyl, haloalkyl, cycloalkylalkyl, alkylcycloalkyl, alkylcycloalkenyl and alkoxycarbonyl; wherein R₆ and R₇ may further be taken together to form a carbocyclic ring consisting of from three to about eight ring members, or to form an imidazolyl or imidazolylalkyl group; and wherein any of the foregoing R₁ through R₇ substituents having a substitutable position may be substituted with one or more groups selected from alkyl, alkoxy, halo, haloalkyl, alkenyl, alkynyl and cyano; or a pharmaceutically-acceptable salt thereof.

10. The method of claim 9 wherein R₁ is selected from imidazolyl, imidazolylmethyl and imidazolylethyl; wherein each of R₂ and R₄ is independently selected from hydrido and lower alkyl; wherein R₃ is selected from hydrido, alkyl, alkoxyalkyl, alkylthioalkyl, imidazolyl, imidazolylmethyl and imidazolylethyl; wherein R₅ is selected from substituted or unsubstituted lower alkyl, cycloalkylalkyl and phenylalkyl; wherein R₆ is selected from hydrido, hydroxy, alkoxy, amino, alkylamino and dialkylamino; wherein R₇ is selected from hydrido, alkyl, haloalkyl, cycloalkylalkyl, alkylcycloalkyl, alkylcycloalkenyl and alkoxycarbonyl; wherein R₆ and R₇ may further be taken together to form a carbocyclic ring consisting of from three to about six members, or to form an imidazolyl, imidazolylmethyl or imidazolylethyl group; and wherein any of the foregoing R₁ through R₇ substituents having a substitutable position may be substituted with one or more groups selected from alkyl, alkoxy, halo, haloalkyl, alkenyl, alkynyl and cyano; or a pharmaceutically-acceptable salt thereof.

11. The method of claim 10 wherein each of R₂ and R₄ is independently selected from hydrido and methyl; wherein R₃ is selected from hydrido, methyl, ethyl, methoxymethyl, methylthiomethyl, imidazolyl and imidazolylmethyl; wherein R₅ is selected from benzyl, cyclohexylmethyl, isobutyl and n-butyl; wherein R₆ is selected from hydrido, hydroxy, methoxy and dialkylamino; wherein R₇ is selected from isobutyl, ethyl, propyl and benzyl; and wherein R₆ and R₇ may be taken together to form a carbocyclic ring consisting of from three to about six members, or to form imidazolyl or imidazolylmethyl; or a pharmaceutically-acceptable salt thereof.

12. The method of claim 11 wherein each of R₂ and R₄ is independently selected from hydrido and methyl; wherein R₃ is selected from methyl and ethyl; wherein R₅ is cyclohexylmethyl; wherein R₆ is hydroxy; and wherein R₇ is selected from isobutyl and ethyl; or a pharmaceutically-acceptable salt thereof.

* * * * *